United States Patent [19]

Watanabe

[11] Patent Number: 4,946,462

[45] Date of Patent: Aug. 7, 1990

[54] ARTHROSCOPIC GUIDE AND METHOD

[76] Inventor: Robert S. Watanabe, 11645 Wilshire Blvd., Ste. 701, Los Angeles, Calif. 90025

[21] Appl. No.: 283,495

[22] Filed: Dec. 12, 1988

[51] Int. Cl.⁵ .............................................. A61B 17/00
[52] U.S. Cl. .................................. 606/148; 606/138; 606/103; 128/898
[58] Field of Search ................. 606/103, 144, 96, 148, 606/138, 898

[56] References Cited

U.S. PATENT DOCUMENTS

| 2,833,284 | 5/1958 | Springer | 606/103 |
|---|---|---|---|
| 4,172,458 | 10/1979 | Pereyra | 606/144 |
| 4,450,835 | 5/1984 | Asnis et al. | 606/96 |
| 4,461,281 | 7/1984 | Carson | |
| 4,580,563 | 4/1986 | Gross | |
| 4,622,960 | 11/1986 | Tam | 606/103 |
| 4,643,178 | 2/1987 | Nastari et al. | 606/103 |
| 4,712,542 | 12/1987 | Daniel et al. | 606/96 |
| 4,796,626 | 1/1989 | Devries | 606/148 |

Primary Examiner—Randall L. Green
Assistant Examiner—Gary Jackson

[57] ABSTRACT

A guide and method for use in arthroscopic knee surgery for the repair and reconstruction of the anterior cruciate ligament. The guide is in the form of a elongated flexible wire, and it enables the semitendinosus and the gracilas tendons to be pulled through the knee joint in an expeditious manner in order to replace the anterior cruciate ligament.

9 Claims, 2 Drawing Sheets

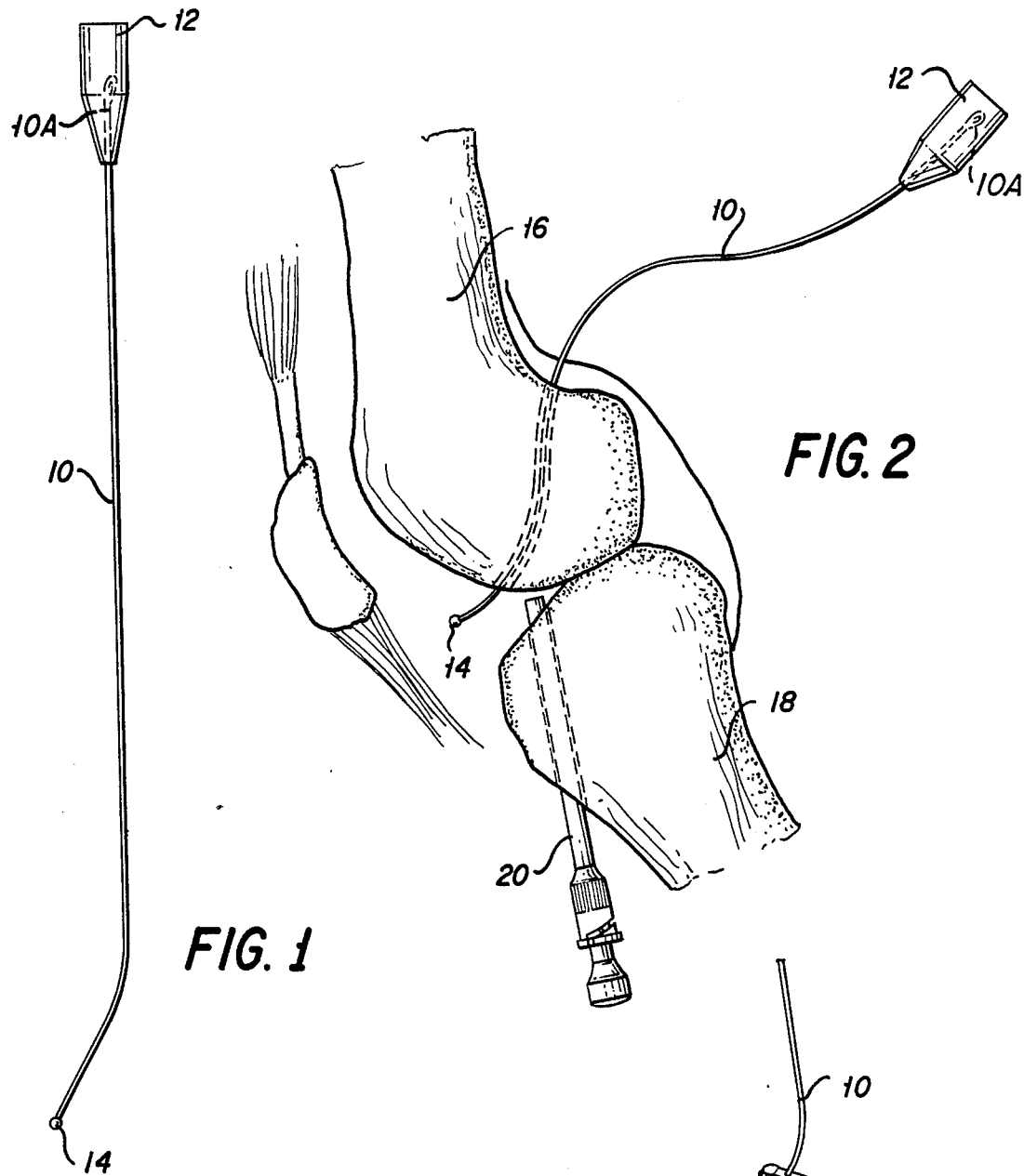

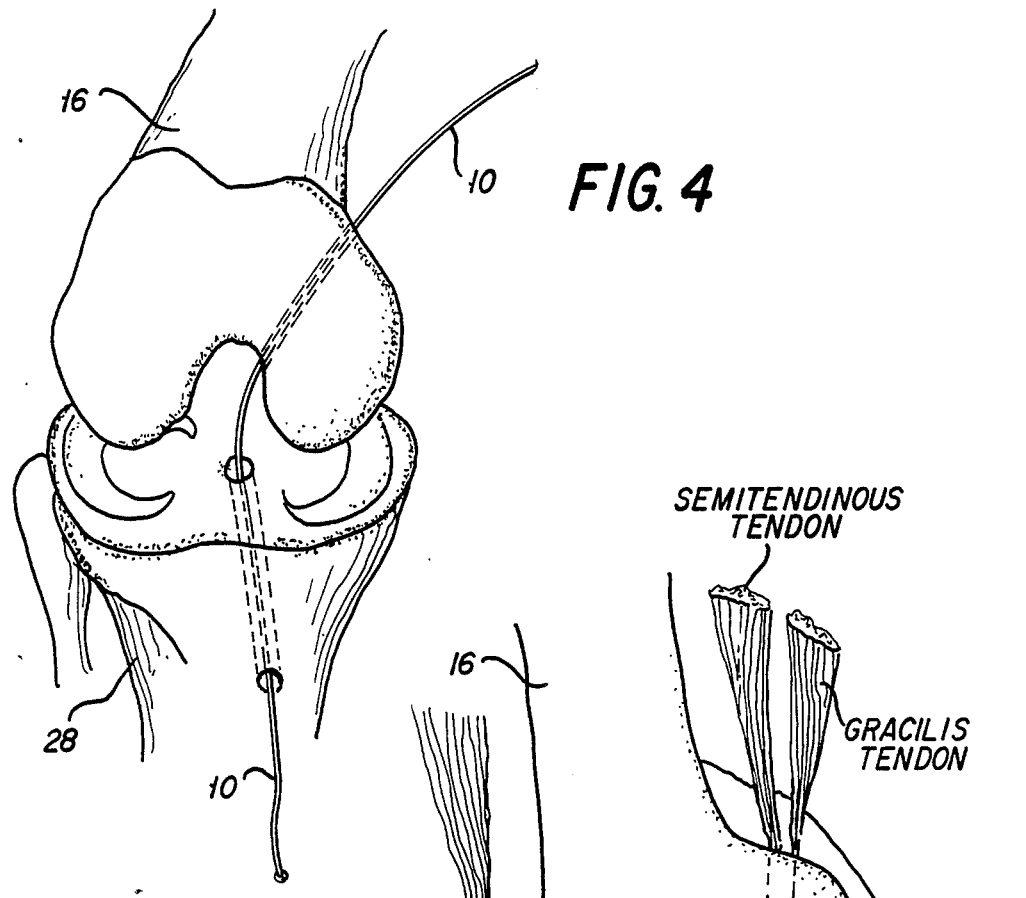
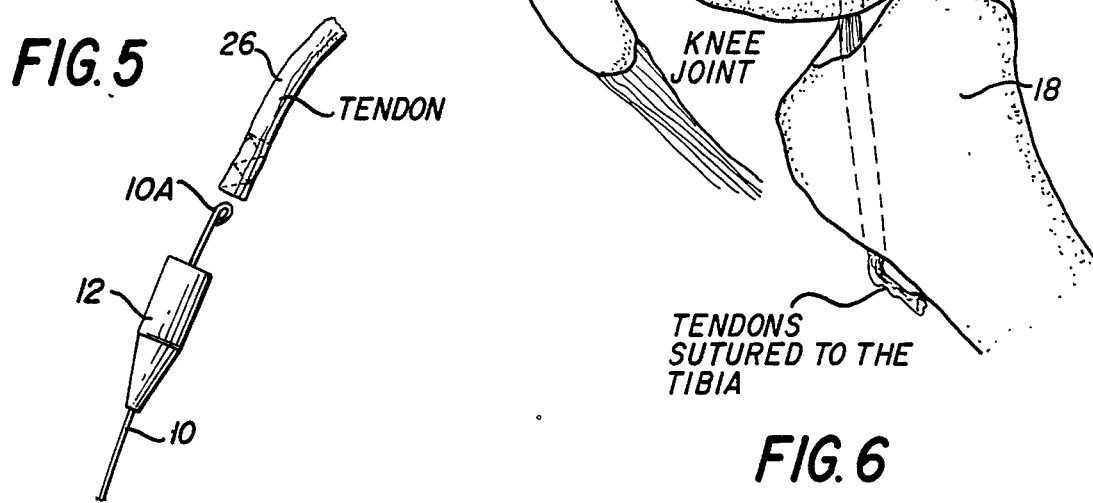

ARTHROSCOPIC GUIDE AND METHOD

BACKGROUND OF THE INVENTION

A knee which exhibits a deficiency in the anterior cruciate ligament presents one of the most difficult problems in the field of sports medicine. Many surgical procedures have been made available in the prior art for the repair and reconstruction of the anterior cruciate ligament. A number of such surgical procedures are presently being performed by arthroscopic techniques in order to eliminate the requirement for large incisions, prolonged hospitalization and prolonged rehabilitation.

The guide of the present invention is particularly intended for use in an arthroscopic surgical procedure for the reconstruction of the anterior cruciate ligament which involves transplanting the semitendinosus and gracilis tendons through the knee joint in order to replace a deficient ligament. In carrying out the procedure, the two tendons are passed through the posterior capsule in the back of the knee, through a hole in the femur into the knee joint, and then through a hole in the tibia. Present prior art instruments are not particularly suitable for this procedure and, as a result, considerable time and effort are wasted by the surgeon in attempting to pass the tendons through the knee joint.

An objective of the present invention is to provide a guide which is particularly suited for pulling the semitendinosus and gracilis tendons through holes in the femur and tibia and through the knee joint in a quick and expeditious manner.

SUMMARY OF THE INVENTION

The guide of the invention consists of a flexible wire having a small ball mounted on the tip of one end, and having a plastic cone mounted on the other end. In the use of the guide, the ends of the semitendinosus and gracilis tendons are sutured to a loop provided in the wire and the cone is slipped up over the sutured ends to act as a cover. The wire is bent to manipulate its tip into an elongated tubular receiver which is inserted into a hole in the tibia. The movements of the tip of the wire may be observed by an appropriate arthroscope while the tip is being manipulated into the receiver by a small wire grasper. The receiver is then pulled out of the tibia which causes the wire and the attached tendons to be pulled through the knee joint.

BRIEF DESCRIPTION OF THE DRAWINGS

FIG. 1 is a side elevational view of a guide constructed to incorporate the concepts of the invention in one of its embodiments;

FIG. 2 is a schematic representation of a knee joint, and an illustration of the manner in which the guide of FIG. 1 is pulled through the knee joint;

FIG. 3 is a fragmentary view showing how the end of the guide is grasped by a wire grasper to manipulate it into a tubular cannula-type receiver;

FIG. 4 is a schematic representation of the knee joint with the guide of FIG. 1 extending through the knee joint;

FIG. 5 is a schematic representation showing the manner in which a tendon may be attached to one end of the guide; and FIG. 6 is a schematic representation of the completed procedure, with the semitendinosus and gracilis tendons extending through the knee joint and sutured to the tibia.

DETAILED DESCRIPTION OF THE ILLUSTRATED EMBODIMENT

As shown in FIG. 1, the guide of the invention consists of an elongated flexible wire 10. A plastic cone is slidably mounted on one end of the wire, and a small ball 14 is attached to the other end. A loop 10A is provided in the end of the wire to permit the tendons to be sutured to the guide.

As shown in FIG. 2, in performing the procedure, a hole is drilled in the middle of the capsule in the back of the femur 16 of the patient, and a second hole is drilled in the tibia 18. A cannula-type receiver 20 is inserted through the hole in the tibia, as shown in FIG. 2, and the guide 10 is inserted through the posterior capsule of the knee and through the hole in the femur.

Assisted by an arthroscope, the guide 10 is grasped by a small wire grasper 24 and its lower end is guided into the receiver 20. The guide is moved down into the receiver, until the ball 14 latches onto a pocket in the receiver which holds the guide in the receiver.

The receiver is then pulled out of the hole in the tibia, causing the guide to be pulled through the knee joint, as shown in FIG. 4.

One or both of the semitendinosus and gracilas tendons, as represented by a tendon 26 in FIG. 5, is then inserted into the plastic cone 12 and sutured to the loop 10A at the end of the wire 10. The plastic cone 12 is then slipped up over the loop and sutured ends of the tendon, and it acts as a cover. Then, the tendon is pulled through the hole in the femur and in the tibia, as shown in FIG. 6, and the lower end of the tendon is sutured to the tibia, as shown. Both tendons may be pulled at the same time through the knee joint and sutured in place, as shown in FIG. 6.

The guide of the invention, and the method illustrated and described, constitutes a simple and expeditious arthroscopic receiver for transplanting the semitendinosus and gracilas tendons through the knee joint in order to replace the deficient anterior cruciate ligament.

It will be appreciated that while a particular embodiment of the invention has been shown and described, modifications may be made. It is intended in the claims to cover all modifications which come within the true spirit and scope of the invention.

I claim:

1. A guide for use in arthroscopic knee surgery for the repair and reconstruction of the anterior cruciate ligament comprising: an elongated flexible wire, means attached to one end of the wire for receiving the end of a tendon to be pulled through the patient's knee by the guide and a receiver for receiving the other end of the wire to facilitate pulling the wire and tendon through the knee joint.

2. The guide defined in claim 1, in which said means has a loop formed at said one end of the wire to permit the tendon to be sutured thereto.

3. The guide defined in claim 2, and which includes a plastic cone slidably mounted on said wire to serve as a cover for the loop and sutured tendon.

4. The guide defined in claim 1, in which said receiver is of the cannula type, and which includes a ball mounted on the other end of the wire to permit the wire to be inserted and held into said cannula-type receiver.

5. A method for implanting a tendon into the knee joint of a patient which comprises drilling holes in the capsule of the femur and tibia, affixing the tendon to one end of a flexible wire, passing the flexible wire through one of the holes, passing a receiver through the other of the holes, manipulating the other end of the wire into the receiver, and pulling the receiver out of the other hole to cause the tendon to pass through the holes and through the knee joint.

6. The method defined in claim 5, in which comprises the step of pulling the tendon until its end protrudes through the hole in the tibia, and suturing the protruding end of the tendon to the tibia.

7. The method defined in claim 5, in which the receiver is of the cannula type, and which includes the step of inserting the wire through the hole in the femur, inserting the cannula-type receiver through the hole in the tibia, and pulling the receiver out of the hole in the tibia to pull the wire and tendon through the knee joint.

8. The method defined in claim 5, and which includes the step of using a wire grasper to manipulate the end of the wire into the receiver.

9. The method defined in claim 7, and which comprises the step of pulling the tendon until its end protrudes through the hole in the tibia, and suturing the protruding end of the tendon to the tibia.

* * * * *